United States Patent

Bandurski et al.

[11] Patent Number: 4,919,893
[45] Date of Patent: Apr. 24, 1990

[54] THERMAL EXTRACTION/PYROLYSIS GAS CHROMATOGRAPH

[75] Inventors: Eric L. Bandurski; Phach F. N. Vu; Gary D. Bruce, all of Tulsa, Okla.

[73] Assignee: Amoco Corporation, Chicago, Ill.

[21] Appl. No.: 201,132

[22] Filed: May 31, 1988

[51] Int. Cl.$^5$ ............................................. G01N 31/12
[52] U.S. Cl. ...................................................... 422/78
[58] Field of Search .................................. 422/78–82; 436/155–160

[56] References Cited

U.S. PATENT DOCUMENTS

| | | | |
|---|---|---|---|
| 3,475,131 | 10/1969 | Keulemans | 422/80 |
| 4,244,917 | 1/1981 | Woods et al. | 422/78 |
| 4,357,836 | 11/1982 | Kokesh | 73/863.11 |
| 4,519,983 | 5/1985 | Espitalie et al. | 422/78 |
| 4,710,354 | 12/1987 | Behar et al. | 422/80 |

FOREIGN PATENT DOCUMENTS 2161269 1/1986 United Kingdom .

OTHER PUBLICATIONS

Wright & Dawes, "Applications of a Continuous Mode Pyrolyzing Inlet for GC", *American Laboratory*, pp. 92–101 (11/86).
"Pyran Systems", Ruska Laboratories, Inc., (1987).
"Instrumentation '87", *Chemical & Engineering News*, 3/23/87.
"Combined Thermal Extraction Gas Chromatography/Pyrolysis Gas Chromatography", GeoLab Info.
Wampler & Levy, "Reproducibility in Pyrolysis Recent Developments", *Journal of Analytical and Applied Pyrolysis*, 12 (1987), 75–82.

*Primary Examiner*—Christine M. Nucker
*Assistant Examiner*—T. J. Wallen

[57] ABSTRACT

A gas chromatograph is converted into a thermal extraction pyrolysis gas chromatograph by adding a temperature progarmmable sleeve around the injection column. Minimal modification to existing nonthermal extraction/nonpyrolysis gas chromatographs is required.

2 Claims, 4 Drawing Sheets

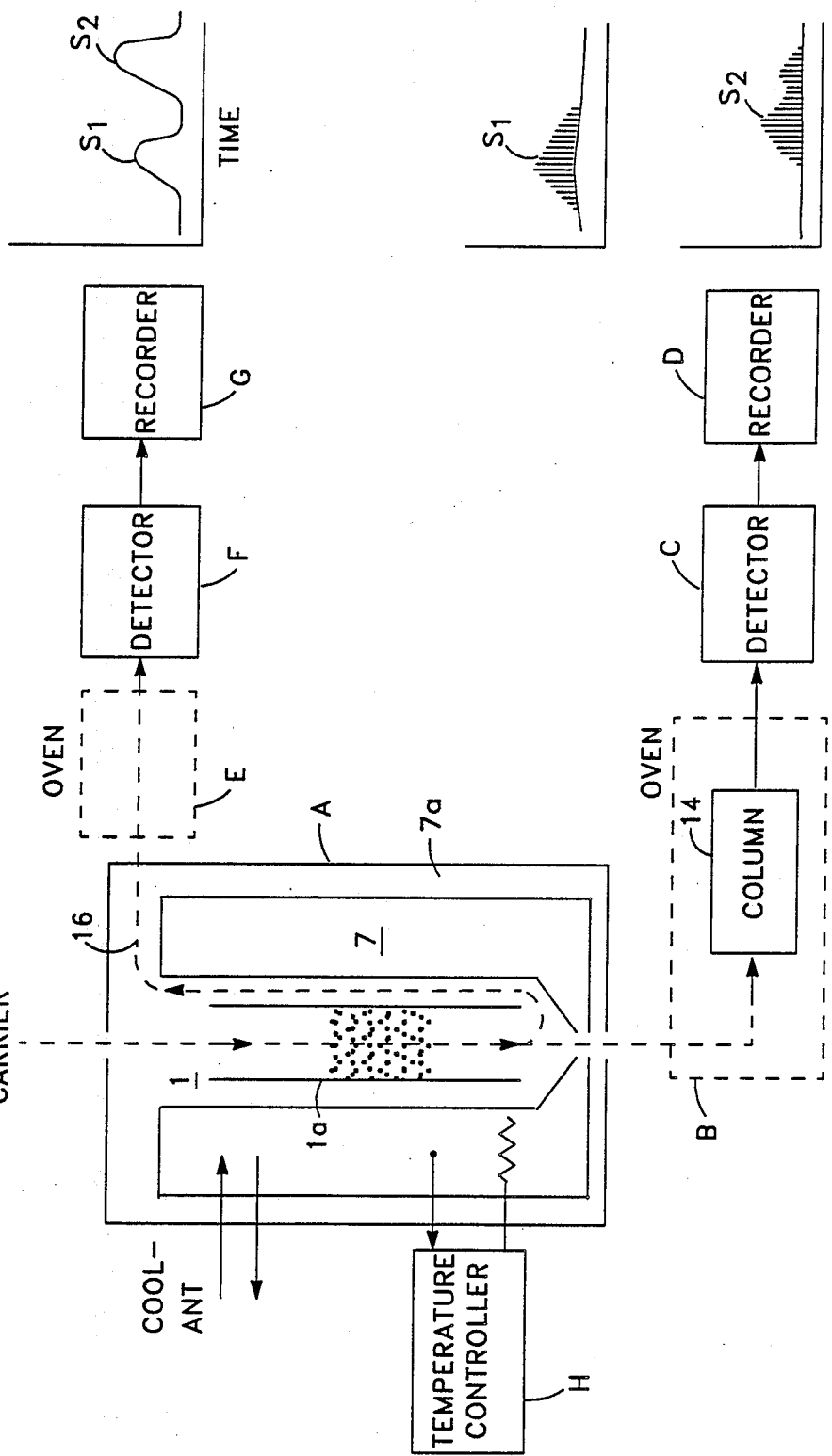

THERMAL EXTRACTION/PYROLYSIS GAS CHROMATOGRAPH

FIELD OF THE INVENTION

The invention relates to thermal extraction/pyrolysis gas chromatography. In a particular aspect, the invention relates to method and apparatus useful for such analysis of geological samples to obtain information useful in petroleum exploration.

SETTING OF THE INVENTION

Thermal extraction gas chromatography and pyrolysis gas chromatography are techniques for analyzing respectively volatile materials and thermally degradable compounds, usually polymers, by controlled heating of a sample followed by gas chromatography of the evolved gases.

In the petroleum industry, thermal extraction gas chromatography is used to isolate and analyze volatile hydrocarbons in rocks, including the lighter components which can be lost during solvent extraction. Pyrolysis gas chromatography is used to determine the kind of hydrocarbons, for example, oil or gas which can be generated from kerogens in rock samples when they are heated. Both thermal extraction and pyrolysis gas chromatography can be used for the same sample, in which case it is desirable to produce a continuous record as a function of time, showing the amount of volatiles released (conventionally designated as $S_1$) and pyrolysates evolved, (conventionally designated $S_2$) preparatory to thermal extract and pyrolysate gas chromatographic analysis.

Currently used or available thermal extraction and pyrolysis gas chromatographs fall into the following classes: (1) Add-On or Front-End Systems in which a furnace for vaporizing and pyrolyzing samples is added and the resulting products are then provided to an existing gas chromatographic inlet (see, Wright and Dawes, "Applications of a Continuous Mode Pyrolyzing Inlet for GC," *American Laboratory*, pages 92–101 (November 1986); (2) Inlet Replacement Systems in which the gas chromatographic inlet is removed and a pyrolyzing injection system is installed in its place (see U.S. Pat. No. 4,357,836); and (3) Stand Alone Systems which contain pyrolyzer, gas chromatograph, and sometimes a data system (see "Pyran System," Ruska Laboratories, Inc. (1987); GB2 161 269 A; Chemical and Engineering News, Mar. 23, 1987; and "Combined Thermal Extraction Gas Chromatography/Pyrolysis Gas Chromatography," GeoLab Info). See also, Wampler and Levy, "Reproducibility in Pyrolysis Recent Developments," J. An. App. Pyrolysis 75–82 (1987).

Systems of type (3) are typically very expensive. Systems of type (1) and type (2) involve modification to the sample flow path of the gas chromatograph. This is disadvantageous since modern conventional gas chromatographs are carefully designed and built for ensuring that the injected sample is effectively delivered to the gas chromatographic column. The geometry of the flow path from the inlet system to the chromatographic column is designed and thermally controlled to avoid traps for sample components resulting from path geometry or from temperature anomalies. In this way, highly representative gas chromatographic analysis of injected samples can be obtained. Systems of types (1) and (2) above, however, require modifications to the flow path of conventional gas chromatographs.

SUMMARY OF THE INVENTION

It has been discovered that commercially available gas chromatographs can be converted into thermal extraction/pyrolysis gas chromatographs by replacing certain elements of the existing gas chromatographic system with elements for generation and control of thermal extraction and pyrolyzing temperatures while maintaining the sample flow path of the existing gas chromatograph substantially intact and unmodified.

According to the invention, there is provided a method for converting a gas chromatograph into a thermal extraction/pyrolysis gas chromatograph. The gas chromatograph comprises an inlet assembly with an insert chamber for receiving a sample insert therein and a heater for controlling the temperature of the inlet assembly. The gas chromatograph also comprises flow directing means for flowing carrier gas through the sample insert and from the inlet assembly to a gas chromatographic column and associated detector(s). The invented method comprises replacing the heater with a temperature control assembly comprising a heater for controllably heating the sample insert therein to thermal extraction and pyrolyzing temperatures and cooling means for controlling temperature and for returning the inlet assembly to initial-state operation between samples. The resulting modified thermal extraction/pyrolysis gas chromatograph maintains the fluid flow path of the existing gas chromatograph substantially intact and unmodified.

According to a further aspect of the invention, there is provided a kit for modifying a gas chromatograph into a thermal extraction pyrolysis gas chromatograph. The kit comprises a temperature control assembly adapted for replacing a heater adjacent an insert chamber for receiving a sample insert in a gas chromatograph. The temperature control assembly comprises a heater for controllably heating a sample insert in the insert chamber to thermal extraction and pyrolysis temperatures, and cooling means for controlling the temperature and for returning the inlet assembly of the gas chromatograph to initial-state between samples. The components of the kit are further adapted to the existing gas chromatograph for maintaining the existing fluid flow path of the gas chromatograph substantially intact and unmodified.

Thus, there is provided means and method for converting a gas chromatograph into a thermal extraction/pyrolysis gas chromatograph by adding a temperature programmable and controllable sleeve having both heating and cooling capabilities around the inlet assembly. The invention requires minimal modification to existing nonthermal extraction/nonpyrolysis gas chromatographs for conversion into thermal extraction/pyrolysis gas chromatographs and is less expensive than commercially available thermal extraction/pyrolysis gas chromatographs.

BRIEF DESCRIPTION OF THE DRAWINGS

The invention will be further appreciated and understood from the drawings in which:

FIG. 4 represents schematically a system for thermal extraction/pyrolysis gas chromatograph embodying the invention.

DETAILED DESCRIPTION OF THE INVENTION

The invented method and article of manufacture provides substantial benefit over currently available devices. Compared to Add-On or Inlet Replacement Systems described above, the invention provides a substantial improvement in technical performance due to the fact that the existing flow path of the gas chromatograph is maintained substantially intact. In comparison with Stand Alone Systems, there is a substantial reduction in cost and increased availability to the industry. Typical Stand Alone Systems can cost, if available commercially, for example on the order of $150,000. To the contrary, a kit in accordance with the invention can be manufactured for about $1500 or less, which when added to the cost of a conventional gas chromatograph, such as, for example, $8000, brings the total cost of the system to about $9500 (1988 $).

In addition to requiring minimal (and reversible) modifications of existing gas chromatographs, and not interfering with the existing gas flow arrangement of commercial capillary inlet systems, a thermal extraction pyrolysis gas chromatograph in accordance with the invention provides the following advantages:

1. A full range of analysis of volatiles or pyrolysates from approximately $C_4$ to $>C_{45}$;
2. Rugged, simple and clean;
3. Spent sample and sample insert can be removed after each analysis to avoid cross contamination;
4. Comparable to the best in quality of thermal extraction pyrolysis gas chromatographic equipment;
5. Reproducible;
6. Compact since the installation is within an existing gas chromatograph;
7. Temperature range is from cryogenic to approximately 600° C. temperature control for the gas chromatographic inlet;
8. Can be used for samples from 1 milligram (mg) up to about 200 mg of rock.

Figure 1:
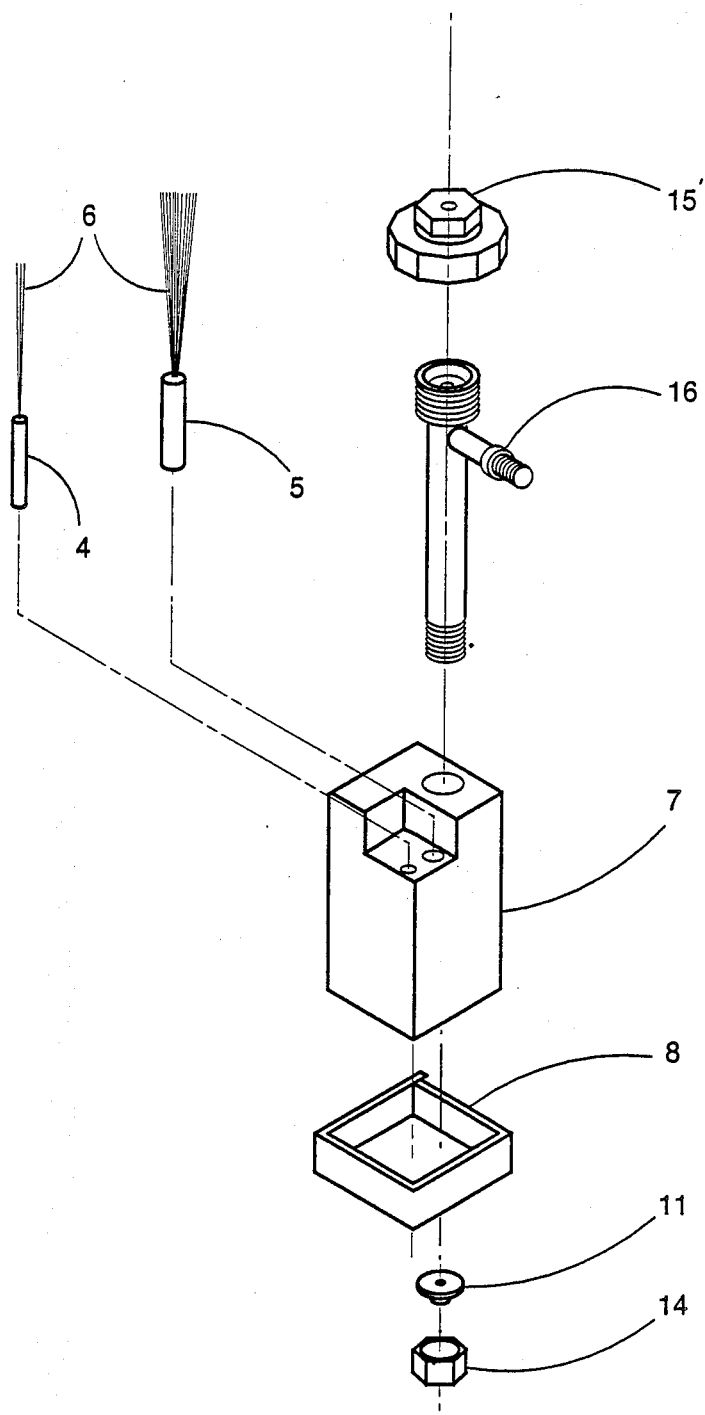
FIG. 1, labeled "Prior Art" represents a simplified exploded view of an inlet system of an existing gas chromatograph.

Referring now to FIG. 1 labeled "Prior Art," FIG. 1 illustrates a simplified exploded view of an inlet system of an existing gas chromatograph. The inlet system comprises an inlet assembly which is adapted for receiving a split flow sample insert illustrated schematically as 1'a adjacent the inlet chamber 1'. The inlet assembly comprises the inlet chamber 1', having an upper opening for placing the sample insert 1'a therein, and an upper cap 15'. Upper cap 15' is equipped with a central orifice through which a sample can be injected through an internal septum not illustrated. The assembly in addition to a carrier gas inlet and a septum purge outlet (not shown in FIG. 1, see FIG. 3) has a split vent outlet 16', and a lower opening with seal 11' and nut 13' for flowingly connecting the upper end of column 14' with the inlet chamber 1'. Inlet chamber 1', with insulation (not shown), is received in a heating block 7' also receives a temperature sensitive element 4' therein for sensing the temperature of block 7' and heating element 5'. Block 7' is received in insulation 8' and has an outlet cooperating with the lower outlet of the chamber 1' for providing carrier gas containing sample components via seal 11' to chromatographic column 14'.

Figure 2:
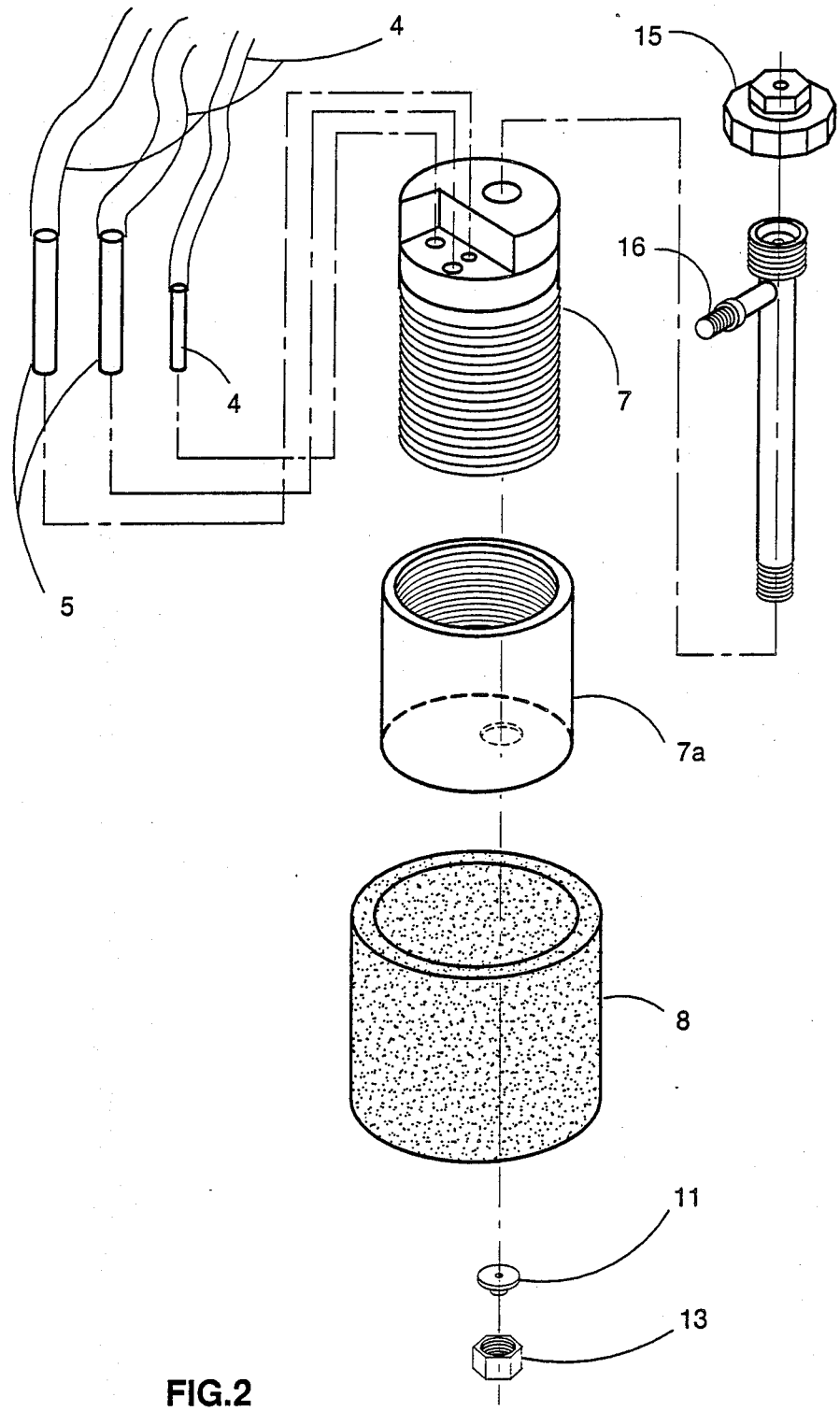
FIG. 2 represents a simplified exploded view of the inlet system of FIG. 1 modified in accordance with the invention.

Referring now to FIG. 2, FIG. 2 illustrates a simplified exploded view of an inlet system of a gas chromatograph modified in accordance with the invention. It can be seen that the heating element 7' and insulation 8' of FIG. 1 are replaced by heating block 7, cooling bath 7a, and modified insulation 8.

Figure 3:
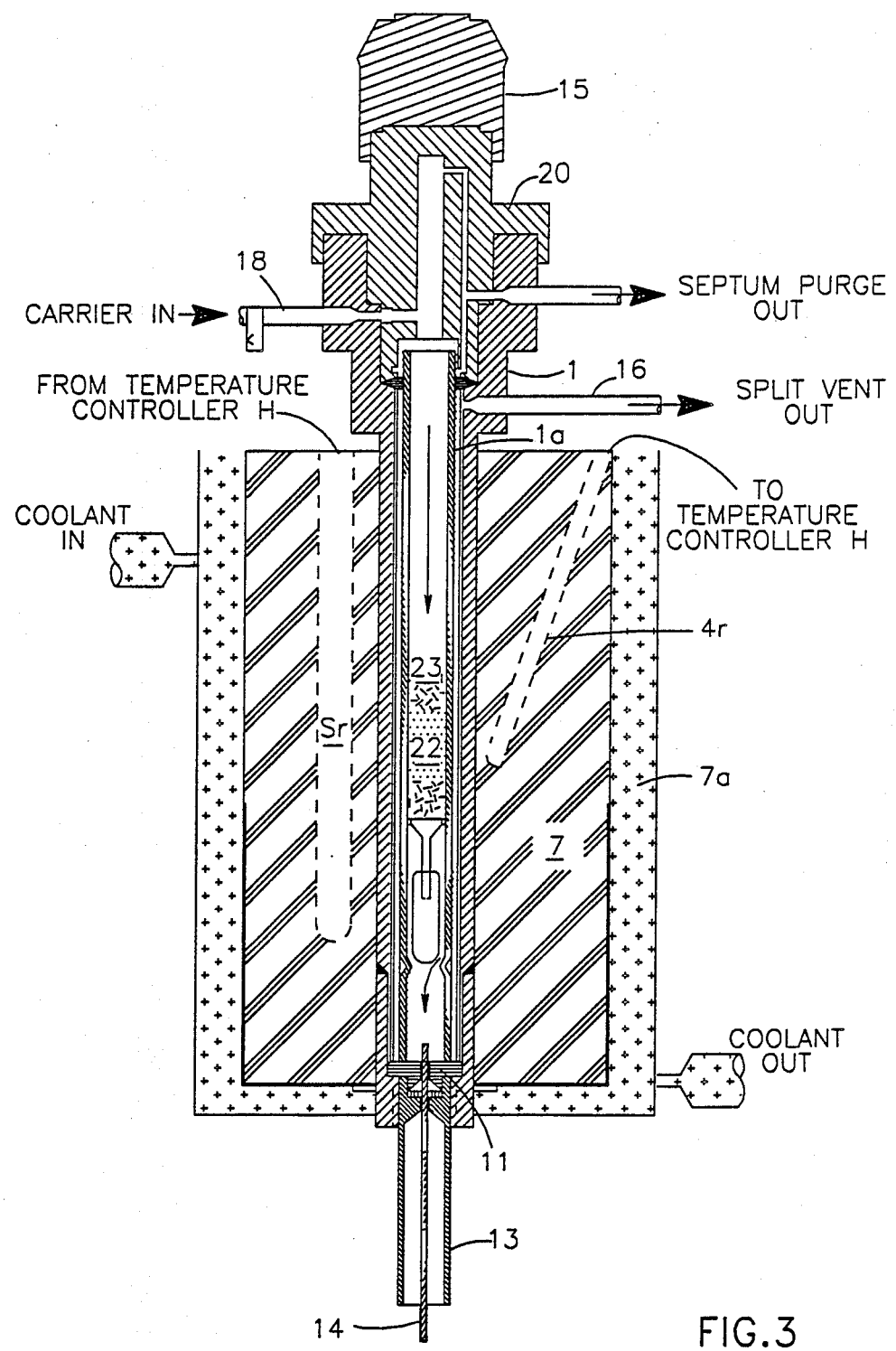
FIG. 3 represents schematically in cross section the inlet system of a thermal extraction/pyrolysis gas chromatograph modified in accordance with the invention.

Heating block 7 can be formed by machining or molding from a thermally conductive metal such as brass, copper, aluminum, or even stainless steel, and the like. Heating block 7 as shown in FIG. 2 is adapted to receive additional capacity heating elements, illustrated by multiple element 5, for generating temperatures effective for thermal extraction and pyrolysis of samples placed in chamber 1. Heating block 7 is adapted to receive inlet chamber 1 in the same manner as heating block 7' receives the inlet chamber 1' shown in FIG. 1, and therefore does not involve modification to the sample flow path. Heating block 7 is also preferably provided with increased heat transfer surface, for example, a ridged or fluted surface as illustrated for facilitating heat transfer when in contact with cooling means 7a, for example, a cooling bath having coolant in and coolant out ports as shown in FIG. 3 for liquid carbon dioxide or liquid nitrogen or the like. Suitable insulation 8 for the cooling bath is also provided to isolate thermally the effect of the inlet assembly from remaining portions of the gas chromatograph. Cap 15 is preferably a solid cap having no orifice therethrough, or alternatively the septum (See discussion of FIG. 1 above) can be removed and replaced with a nonthermally degradable material such as a graphite seal which can withstand pyrolysis temperatures as high as 600° C. Other reference numerals correspond to those used in FIG. 1 and need not be further described here.

Referring now to FIG. 3, FIG. 3 illustrates schematically in cross section the inlet system of a thermal extraction/pyrolysis gas chromatograph modified in accordance with the invention. As illustrated in FIG. 3, the sample chamber can be of the type having a carrier inlet 18 and a split vent outlet 16. The structures defining the flow of the septum purge gas are illustrated as a single structure 20 for simplicity. The flow path is illustrated schematically in FIG. 4. Sample chamber 1 receives a sample insert 1a having a sample 22 contained therein with glass wool 23 above and below. Insert 1a is preferably of a conventional split flow design which when received in sample chamber 1 allows a portion of the carrier gas to pass to chromatographic column 14, while the remaining portion of carrier gas also containing sample components and substantially under the same conditions passes through an annulus adjacent insert 1a to split vent outlet 16. The flow path is illustrated schematically in FIG. 4. The temperature of the inlet chamber 1 is controlled by heating block 7, having one or more receptacles 5r for heating elements 5 and one or more receptacles 4r for temperature sensors. A separate sensor for causing the heaters to shut off at a critical upper threshold, for example, approximately 600° C. can be employed. Preferably, the temperature sensor 4 is inserted at an angle from vertical so that the thermal sensor is closely adjacent the inlet chamber 1 for accurate sensing of the temperature of the inlet chamber 1. Heating assembly 7 is heated by heating elements 5 under the control of a temperature controller H (see FIG. 4). Cooling bath 7a is also under control of a temperature controller such as H in FIG. 4.

Referring now to FIG. 4, FIG. 4 illustrates schematically a system for thermal extraction/gas chromatography embodying the invention. As illustrated the system comprises a sample inlet assembly A which comprises a heating block 7 and a colling bath 7a under temperature control of temperature controller H. Temperature controller H can be, for example, a programmable temperature controller, for example, Omega Model CN-2010 available from Omega Engineering Inc., Stamford, Conn. suitable for controllably increasing the temperature of the heating block 7 in discrete time-controllable temperature increments. A single programmable temperature controller or more than one can be employed.

A portion of the gas from the inlet chamber 1 can be provided by heated line E to detector F, for example, a flame ionization detector, to recorder G to provide a quantitative record as a function of time of evolved gases from the sample. Line E is maintained at a temperature of about 350° C. to prevent condensation of volatiles or pyrolysate. In the record produced by recorder G, peak $S_1$ *represents volatiles contained in the sample and peak* $S_2$ represents pyrolysates evolved. Another portion of the gas from the inlet chamber 1 is provided to a gas chromatogrpah illustrated by column 14 and a temperature controlled oven B, then provided to a detector C, for example, a flame ionization detector, and to a recorder D to give gas chromatographic resolution of each of the volatile peak $S_1$ and the pyrolysate peak $S_2$. In the analysis recorded by recorder D, as illustrated, the $S_1$ and $S_2$ peaks are chromatographically resolved into individual components.

In the operation of FIG. 4, the heating block 7 can be cooled to approximately 0° C. or less with a luid, such as, liquid nitrogen, cold nitrogen, carbon dioxide, and the like. A sample of between 1 and 200 mg placed in a standard fused silica split flow insert 1a is placed into the cold inlet chamber 1. The top of the inlet can be sealed with nut 15 (not shown) (see FIGS. 1 and 2) and capillary column flow can be reestablished by flowing carrier gas into the inlet chamber 1. The gas chromatographic column 14 under control of the gas chromatographic oven B can be cooled to $-80°$ C. or less to trap volatiles on the column. Then the block 7 can be heated using temperature programmer H to the desired temperature to release volatiles from the sample and/or to pyrolyze the sample. A typical range of operation would be from $-80°$ C. up to about 600° C. The volatiles and/or pyrolysis fragments are transported by carrier gas and trapped at the head of the gas chromatographic column 14, which can be temperature programmed as in a conventional gas chromatographic analysis. A second portion of the gas from the inlet chamber 1 is removed, for example, by the split vent 16 by heated line E for quantitating evolution of volatiles and pyrolysate as a function of time. At the end of a sample run, the insert 1a can be removed and cleaned for use in a subsequent analysis. Since sample inserts are used and a cooling bath is provided around heating element 7, little time is required between sample runs to return the system to initial state conditions.

When utilizing a capillary inlet as a pyrolysis chamber in accordance with the invention, the short length of the gas chromatographic column which is inserted into the inlet is subjected to higher than normal temperatures ($>350°$ C.). This can cause the liquid phase inside the column or the polyimide coating on the outside of certain columns to degrade. Volatile fragments of these coatings can then appear on pyrograms or succeeding thermal extract analyses. These artifacts can be avoided by prepyrolizing the portion of the column which is to be inserted into the inlet chamber 1. This prepyrolysis can be done, for example, in the flame of a Bunsen burner while carrier gas is flowing through the column. The prepyrolyzed portion of the column can then be inserted into the sample chamber, insuring, for example, that the connector is tightened onto the polyimide coated part of the column, if a fused silica column is being used.

It will be appreciated that there has been provided method and article of manufacture for converting a gas chromatograph into a thermal extraction pyrolysis gas chromatograph which requires minimal modification to existing nonthermal extraction/nonpyrolysis gas chromatographs and which is less expensive than commercially available thermal extraction/pyrolysis gas chromatographs.

What is claimed is:

1. A method for converting a nonthermal extraction pyrolysis gas chromatograph into a thermal extraction pyrolysis gas chromatograph, the nonthermal extraction pyrolysis gas chromatograph comprising an inlet assembly with a sample flow path comprising an insert chamber for receiving a sample insert having a sample therein and flow defining means for directing flow of gas through the insert chamber to a gas chromatographic column, and the inlet assembly further comprising a heater for controlling the temperature of the inlet assembly, the method comprising:

adapting a temperature control assembly for replacing the heater in the nonthermal extraction gas chromatograph and for receiving the insert chamber of the nonthermal extraction pyrolysis gas chromatograph without modifying the sample flow path of the nonthermal extraction pyrolysis gas chromatograph, the temperature control assembly comprising a furnace for controllably heating the sample insert to thermal extraction and pyrolysis temperatures and a cooling means for controlling the temperature of the inlet assembly and for returning the temperature of the inlet assembly to initial state conditions following use of the apparatus, replacing the heater with the thus-adapted temperature control assembly, and maintaining the sample flow path of the nonthermal extraction pyrolysis gas chromatograph substantially without modification.

2. The method of claim 1 wherein the step of adapting comprises forming from thermally conductive material a heating block adapted for receiving the sample flow path of the nonthermal extraction pyrolysis gas chromatograph and for receiving therein means for heating the heating block;

providing a cooling bath for cooling the heating block having coolant-in and coolant-out ports, providing insulation for thermally insulating the effects of thermal extraction pyrolysis temperatures of the heating block and cooling bath from remaining portions of the gas chromatograph; and wherein the step of replacing comprises installing the insert chamber of the nonthermal extraction pyrolysis gas chromatograph in the thus provided heating block and maintaining the sample flow path of the nonthermal extraction pyrolysis gas chromatograph substantially without modification and replacing the heater of the nonthermal extraction pyrolysis gas chromatograph with the thus provided heating block, cooling bath, and insulation.

* * * * *